(12) United States Patent
Feng et al.

(10) Patent No.: US 8,343,053 B2
(45) Date of Patent: Jan. 1, 2013

(54) DETECTION OF STRUCTURE IN ULTRASOUND M-MODE IMAGING

(75) Inventors: Shaolei Feng, Plainsboro, NJ (US); Wei Zhang, Falls Church, VA (US); Shaohua Kevin Zhou, Plainsboro, NJ (US); Jin-hyeong Park, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 238 days.

(21) Appl. No.: 12/839,547

(22) Filed: Jul. 20, 2010

(65) Prior Publication Data

US 2011/0021915 A1 Jan. 27, 2011

Related U.S. Application Data

(60) Provisional application No. 61/227,236, filed on Jul. 21, 2009.

(51) Int. Cl.
*A61B 8/00* (2006.01)
*G06K 9/00* (2006.01)
*G06E 1/00* (2006.01)

(52) U.S. Cl. ........... 600/443; 600/437; 382/128; 706/20

(58) Field of Classification Search .................. 600/437, 600/441, 443, 455; 382/128; 706/20
See application file for complete search history.

(56) References Cited

U.S. PATENT DOCUMENTS 5,800,356 A 9/1998 Criton et al.

2006/0122505 A1 6/2006 Dala-Krishna
2007/0196005 A1 8/2007 White et al.
2008/0071711 A1 3/2008 Zhang et al.

OTHER PUBLICATIONS

L Bertelli, R Cucchiara, G Paternostro, A Prati. "A semi-automatic system for segmentation of cardiac M-mode images". Pattern Anal Applic (2006) 9:293-306.*
"Probabilistic Boosting-Tree: Learning Discriminative Models for Classification, Recognition, and Clustering", Zhuowen Tu, ICCV pp. 1589-1592, 2005.
"Fast Automatic Heart Chamber Segmentation from 3D CT Data Using Marginal Space Learning and Steerable Features", Yefeng Zheng, Adrian Barbu, Bogdan Georgescu, Michael Scheuering, and Dorin Comaniciu, 8 pages, ICCV 2007.
"A probabilistic, hierarchical, and discriminant framework for rapid and accurate detection of deformable anatomic structure", S. Kevin Zhou, F. Guo, J.H. Park, G. Carneiro, J. Jackson, M. Brendel, C. Simopoulos, J. Otsuki, and D. Comaniciu, 8 pages, ICCV Oct. 2007.

* cited by examiner

*Primary Examiner* — Michael Rozanski

(57) ABSTRACT

Automated detection of structure is provided in ultrasound M-mode imaging. A coarse and fine search for structure is used. For example, a less noise susceptible initial position or range of positions for a given structure is determined. This position is then refined. The coarse positioning and/or the refined position may use machine-trained classifiers. The positions of other structure may be used in either coarse or fine positioning, such as using a Markov Random Field. The structure or structures may be identified in the M-mode image without user input of a location in the M-mode image or along the line.

19 Claims, 5 Drawing Sheets

DETECTION OF STRUCTURE IN ULTRASOUND M-MODE IMAGING

RELATED APPLICATIONS

The present patent document claims the benefit of the filing date under 35 U.S.C. §119(e) of Provisional U.S. Patent Application Ser. No. 61/227,236, filed Jul. 21, 2009, which is hereby incorporated by reference.

BACKGROUND

The present embodiments relate to medical ultrasound imaging. In particular, structure represented in M-mode imaging is detected and may be used for measuring heart function.

An M-mode echocardiogram is a spatial-temporal image captured using an ultrasound device. Instead of using multiple interrogation beams like B-mode echocardiography, M-mode uses one interrogation beam and captures intensity information of that beam across time. M-mode images may have high image quality, allowing accurate measurement and capture of subtle motion. Due to these characteristics, M-mode imaging is used frequently to image the moving heart of a patient. The functionality of anatomic structures inside the heart, like the left ventricle and aortic root, may be assessed.

To assess the tissue motion, the tissue structure or anatomy is determined from the M-mode image. The sonographer may position calipers at different times, such as the end of diastole or end of systole, to designate tissue structure locations along the scan line at those times. The calipers are used to determine various measurements.

However, manual placement of the calipers may be time consuming and difficult. Ultrasound images may be noisy. Different M-mode images appear different due to different pathologies. The heart size varies for different patients. These sources of variance between M-mode images make placement of the calipers difficult.

BRIEF SUMMARY

By way of introduction, the preferred embodiments described below include methods, computer readable media and systems for automated detection of structure in ultrasound M-mode imaging. A coarse and fine search for structure is used. For example, a less noise susceptible initial position or range of positions for a given structure is determined. This position is then refined. The coarse positioning and/or the refined position may be found using machine-trained classifiers. The positions of other structures may be used, such as using a Markov Random Field, in either coarse or fine positioning. The structure or structures may be identified in the M-mode image without user input of a location in the M-mode image or along the line.

In a first aspect, a method is provided for detection of structure in ultrasound M-mode imaging. M-mode data representing a line within a patient over a range of time is acquired. A portion of the line is identified as associated with a structure of a heart of the patient. The portion includes a plurality of depths and is identified as a function of the M-mode data. A location of the structure within the portion is identified. A search for the identifying of the location is limited to the portion. Information associated with the location, such as a caliper or a measurement, is displayed.

In a second aspect, a non-transitory computer readable storage medium has stored therein data representing instructions executable by a programmed processor for detection of structure in ultrasound M-mode imaging. The storage medium includes instructions for locating, in an M-mode image, first positions of respective structures in a search, the search being based on intensity as a function of depth integrated over a plurality of times and machine-trained feature probabilities. The first positions are refined to second positions of the structures. The refining is limited by the first positions where each of the second positions is a function of a plurality of the first positions. A measurement is calculated as a function of the second positions. The locating and refining are performed free of user input of a location of any structure in the M-mode image.

In a third aspect, a system is provided for detection of structure in ultrasound M-mode imaging. A memory is operable to store ultrasound M-mode data representing a line within a patient over a range of time. A processor is operable to identify a location of the structure from the ultrasound M-mode data and free of user input of any location of any structure along the line. A display is operable to display an M-mode image of the line with the location indicated by a marker, to display a measurement that is a function of the location, or to display the M-mode image of the line with the marker and the measurement.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Fast and accurate detection of anatomical structures in M-mode image may be provided. The structures are detected for position determination and/or placement of calipers. Automated detection may be challenging because of dramatic variations in appearance of any given structure. A rough estimate followed by a constrained or refining search is used to deal with at least some of the challenges. For example, rough caliper localization uses an intensity profile of the M-mode data to deal with noise and/or structure variation. A constrained search is then performed for accurate caliper positions. Markov Random Field (MRF) and warping image detectors may be used for jointly considering appearance information and the geometric relationship between calipers or structure locations.

In one embodiment, the end of diastole (ED) and end of systole (ES) line positions for one or more heart cycles are estimated based on an ECG signal. The system automatically estimates the vertical (i.e., spatial) coordinates of a plurality of calipers along each line (ED and SD lines). The detection of structure along the lines is challenging because the ultrasound M-mode image or data is usually noisy, the M-mode data varies due to differences in pathology, and the heart size varies for different patients. The system addresses this challenging task in a progressive manner. A coarse localization is obtained first using an intensity profile image. Then, precise localization is obtained by considering both the appearance (e.g., M-mode data) and a geometric relationship between those anatomical structures.

Figure 1:
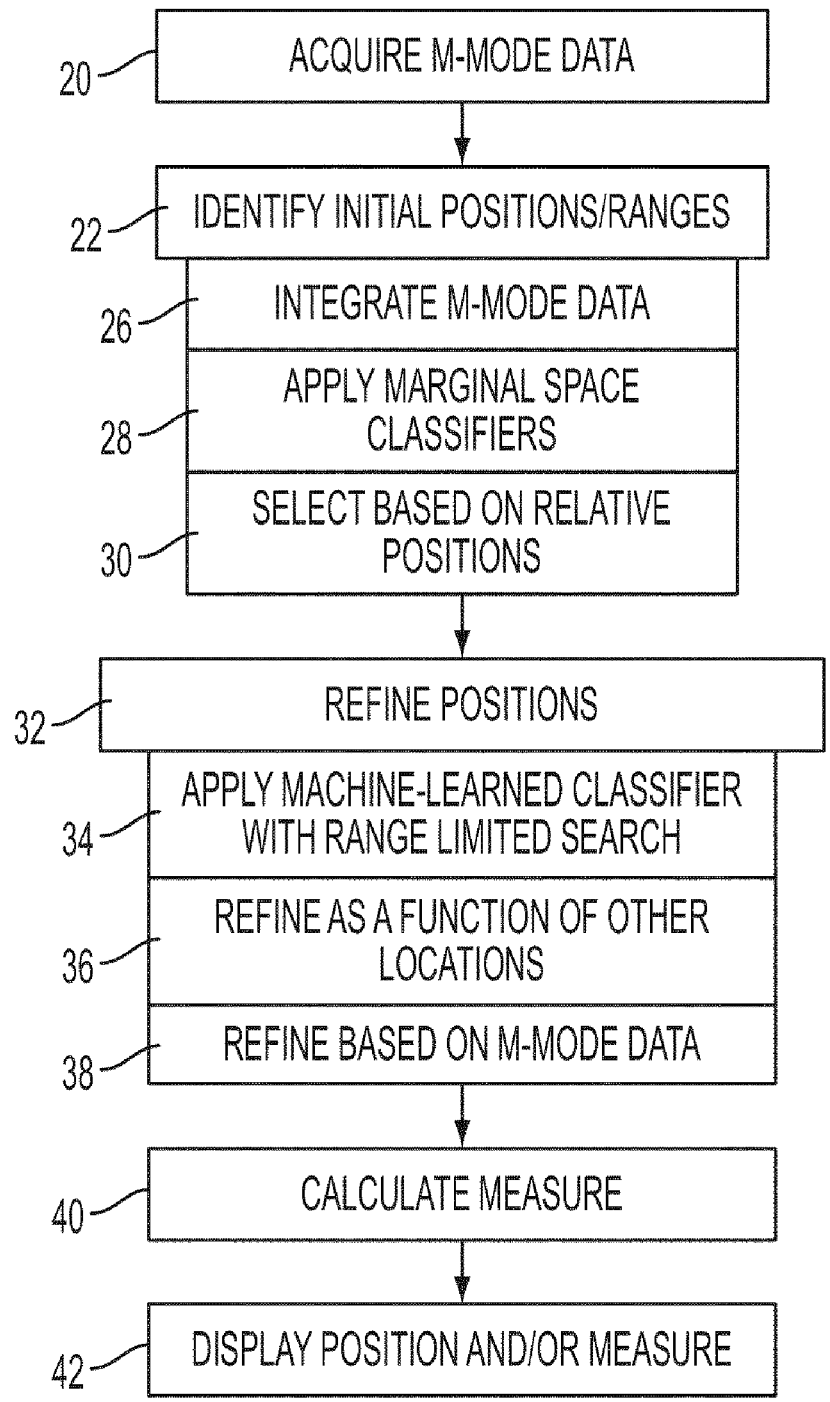
FIG. 1 is a flow chart diagram of one embodiment of a method for detection of structure in ultrasound M-mode imaging.

FIG. 1 shows a method for detection of structure in ultrasound M-mode imaging. The method is implemented by a medical diagnostic imaging system, a review station, a workstation, a computer, a PACS station, a server, combinations thereof, or other device for image processing medical ultrasound data. For example, the system or computer readable media shown in FIG. 7 implements the method, but other systems may be used.

Figure 2:
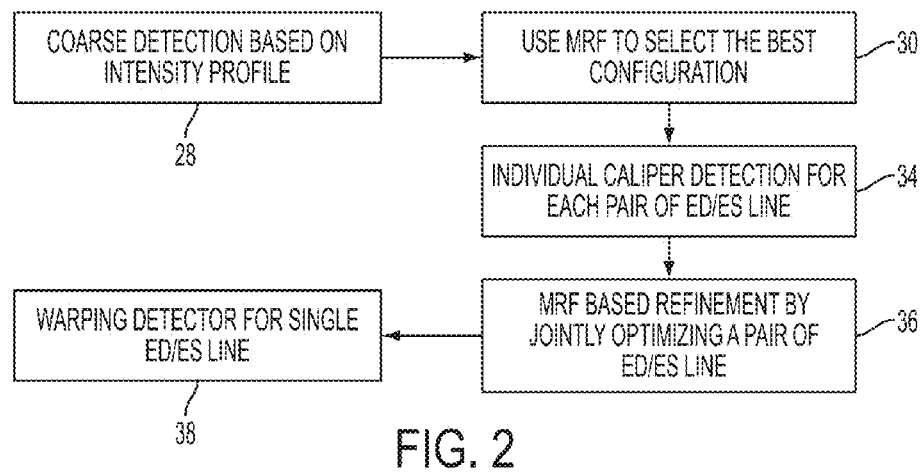
FIG. 2 is a flow chart diagram of another embodiment of a method for detection of structure in ultrasound M-mode imaging.

The method is implemented in the order shown or a different order. Additional, different, or fewer acts may be performed. For example, act 22 is performed without acts 26, 28, and/or 30, and/or act 32 is performed without acts 34, 36, and/or 38. Acts 22 and 32 may include none, one, two, all, or additional sub-acts 26, 28, 30, 34, 36, 38 than shown in FIG. 1. As another example, acts 40 and/or 42 are optional. In yet another example, FIG. 2 represents one specific embodiment of the method of FIG. 1 without general acts 22 or 32. Other embodiments are possible.

The acts are performed in real-time, such as during scanning. The user may view images of act 42 while scanning to acquire another dataset representing intensity or velocity along a line. The images of act 42 are displayed in a scrolling manner along the time dimension with automatically detected calipers and/or measurements. The images may be associated with previous performance of act 20 in the same imaging session, but with different data. For example, act 20 is performed for an initial scan and for subsequent scans during the same imaging session. Measurements and/or images of automatically detected anatomy may be provided in less than one second while additional M-mode data or scans are performed. In alternative embodiments, acts 20-42 may be performed on M-mode data from a previous imaging session, such as stored M-mode data from scans that occurred minutes, hours, days, weeks or longer in the past.

For training and/or application of embodiments using machine-learned classifiers, ultrasound data representing the anatomy of interest, such as a left ventricle or aorta, is used. For training, the data is the same type of data as is going to be used for application. For application, the data is the same type of data as used in the training.

In act 20, M-mode data is acquired. The M-mode data is acquired from a memory, by transfer from memory or over a network, or in real-time with scanning. M-mode data represents a line within a patient over a range of time. For example, transmit and receive ultrasound beams are formed along a scan line. Data is sampled in the receive beam at depths of interest, such as depths corresponding to a patient's heart. The samples are detected. In one embodiment, the samples are detected with an intensity detector. The intensity of echoes represented by the samples is determined and mapped to a grayscale value. In another embodiment, the samples are detected with a Doppler or flow detector. The velocity, power, variance or combinations thereof are estimated and mapped along a color scale.

The scan line is scanned at any repetition rate to acquire data for the temporal dimension. The M-mode scanning may be continuous (e.g., transmit and receive operations with or without a delay for acoustic reverberation die down are performed sequentially without interleaving for other scanning modes) or may be interleaved with B-mode, flow mode or other scanning modes. Each repetition provides data for another time. For each time, samples representing the scan line are provided.

The M-mode data corresponds to a displayed image, detected data prior to scan conversion, scan converted data, data prior to color or grayscale mapping, data mapped for display, beamformed data prior to detection, and/or data at other stages of processing. The M-mode data represents a one-dimensional region of a patient. The region includes tissue, fluid or other structures. Different structures or types of structures react to the acoustic energy differently. The location of the structure along the scan line may be reflected in the M-mode data. For example, the right ventricle internal wall, interventricular septum, left ventricle internal wall, and left ventricle posterior wall for any given time in the heart cycle may be represented.

To detect one or more of these structures at a given time, the method is performed with two modules in a progressive fashion as represented by acts 22 and 32. The first module of act 22 performs coarse detection based on an intensity profile image or other information. The second module of act 32 estimates the precise location of each caliper. In another approach, separate modules are provided for each act or other combinations of acts may be performed. For example, the workflow illustrated in FIG. 2 is used. As yet another approach, one module is provided to perform all of the acts included in a given embodiment.

The coarse detection and precise location estimation (e.g., position identifying acts 22 and 32) are performed without user input of any location along the scan line. The user may activate the M-mode imaging, automated structure detection, and/or automated measurement, but spatial information relative to the M-mode data or image is not provided. The user does not indicate the location of one or more structures for which location is to be determined. The initial locating in act 22 and the refining of act 32 are performed free of user input of a location of any structure in the M-mode image. The user may indicate a depth for which the M-mode scan is to occur, but does not indicate locations within the range of depths within a region of interest. In alternative embodiments, the user indicates the position of one or more structure locations at one or more times.

In act 22, portions of a line associated with one or more different structures are identified. The portions represent initial locations of respective structures identified in a search. A portion corresponds to two or more points along the line. For example, a region of contiguous points along the line likely to represent the structure of interest is a portion. As another example, a couple of non-adjacent or adjacent locations likely to be the structure of interest is a portion. In one embodiment, different portions of the line represented by M-mode data associated with different heart structures are identified. Each point or sample in the portion corresponds to different depths relative to the transducer.

The search is a function of the M-mode data, such as M-mode data from an image to be displayed, being displayed, or previously displayed. The portions are identified from a first estimate of a location of the structure along the line. A window is defined around the given location for the portion. Alternatively, the portions may be identified directly without identification of a specific point.

By identifying a portion alone or based on a point, a coarse or initial detection of the structure is provided. The coarse detection may be more robust in view of noise in an ultrasound image. More processing intensive estimation may be limited to the portion associated with the coarse detection rather than processing all of the data along the scan line. With the coarse detection, the search range for each caliper is constrained during the processing intensive final searching, which increases the detection speed. Moreover, using two stages of detection may make it less likely to get stuck in local maxima for a final location output.

Any coarse search may be used, such as low pass filtering the data as a function of space and applying a threshold. Model matching may be used. A machine-learned classifier using any desired features may be applied.

In one embodiment in act 26, the coarse search is based on intensity as a function of depth integrated over a plurality of times. The M-mode data may be processed prior to integration. For example, color M-mode data is converted to grayscale. As another example, the M-mode data is temporally normalized. The heart cycle of the M-mode data is temporally stretched or compressed using interpolation, decimation, extrapolation, filtering or other process to correspond with a reference heart cycle length in time. Other processes may be performed.

Figure 3:
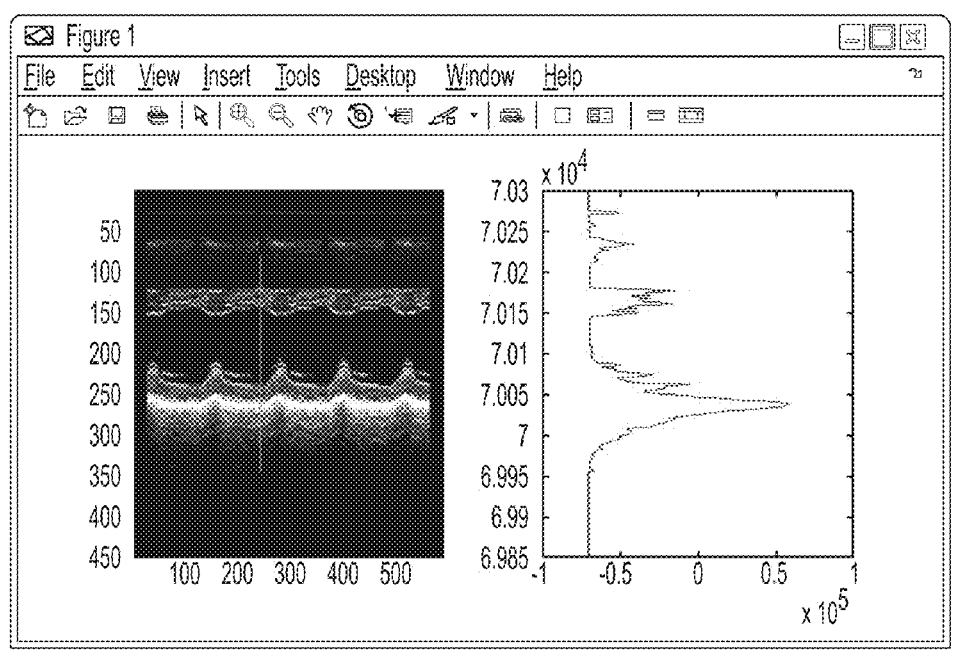
FIG. 3 shows an example M-mode medical image and an integration profile.

Once prepared, the M-mode data is integrated over time. For each depth along the line, the M-mode data over a portion of a heart cycle, a plurality of heart cycles, the time represented in a portion of an image, the time represented over an entire image, user set time frame, or other length of time is summed. FIG. 3 shows an M-mode image with over four heart cycles. The M-mode data for each depth is summed along the entire image, resulting in the intensity profile or curve shown in the right half of FIG. 3. The intensity profile image gives strong cues about the vertical coordinates of each caliper or structure. Other combination functions may be used, such as an average. The combination may reduce the effects of noise.

The intensity profile may be matched to a profile model or thresholds may be applied. The initial locations may be determined from the matched model or thresholds. The portion associated with a given structure is identified from this integrated M-mode data.

Alternatively, in an embodiment represented by act 28, the portion or initial position is identified from the M-mode data by application of a machine-learned classifier. The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used.

The classifier is trained from a training data set using a computer. Any number of expert annotated sets of ultrasound M-mode data is used. For example, about 200 hundred or more ultrasound M-mode images representing the left and/or right ventricles are annotated by expert positioning of one or more calipers. The annotation indicates the location of structures. This large number of annotations allows use of a probabilistic boosting tree to learn relevant features over a large pool of 1D or 2D Haar features. Haar features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning classifier. A database of known cases is collected for machine learning, providing a database-driven knowledge-based approach. Knowledge is embedded in large annotated data repositories where expert clinicians manually indicate the anatomies and/or measurement indicators for the anatomies. Training and detecting the location of measurement indicators include detecting the associated anatomy since the measurement indicator (e.g., caliper) indicates the anatomy. The known cases may be aligned or registered, such as temporal normalization and/or intensity normalization. The detectors are trained on a large number of annotated ultrasound M-mode data sets. The classifier learns various feature vectors for determining the position of portions or an initial estimate of the location of the structure. In alternative embodiments, the classifier is manually programmed.

A probabilistic boosting cascade tree (PBT) unifies classification, recognition, and clustering into one treatment. In one embodiment, a probabilistic boosting tree is learned for each anatomy of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques, such as disclosed by Tu, "Probabilistic Boosting-Tree: Learning Discriminative Models for Classification, Recognition, and Clustering," Proc. Int'l Conf. on Computer Vision, pp 1589-1596, 2005. One classifier may be trained to detect all or some of the structures of interest. In other embodiments, separate classifiers are trained for detecting each of the structures of interest.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies or structures. For example, different classifiers are trained for detecting different portions or initial locations. Each classifier selects a set of discriminative features that are used to distinguish the positive target from negatives. The features are selected from a large pool of features. The large pool is determined by a programmer or may include features systematically determined.

Figure 4:
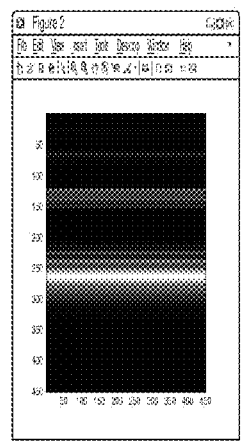
FIG. 4 is an illustration of a two-dimensional projection of the integration profile of FIG. 3.

The machine-trained classifier in one embodiment searches based on machine-trained feature probabilities. For example, a marginal space classifier weights the features with a matrix of feature probabilities to determine an output. FIG. 4 shows an image used to extract the features. The image is a mapping of the intensity profile over time. The one-dimensional profile information is extended along the time dimension. The intensity of each pixel is proportional to the value of the corresponding entry in the intensity profile for that depth. The features, such as 2D (space and time) Haar features, are calculated from the image. Other features may be included or used instead, such as features calculated from the M-mode data prior to integration and/or features calculated from the intensity profile. Other features different than or in addition to Haar features may be used.

For identifying different portions and/or associated initial estimates of different structure locations, separate classifiers are applied using the same or different features. In an alternative embodiment, a joint classifier may be applied. The joint classifier includes different classifiers for different anatomies. For joint classification, at least one of the anatomies is detected as a function of the previous detection of another of the anatomies. The different portions may overlap in depth. Alternatively, the different portions do not overlap.

Acts 26 and 28 may be used alone or together. Act 30 may be used with the output of either to select the most likely position for each structure based on the locations estimated for other structures. Alternatively, act 30 is not performed.

Figure 5:
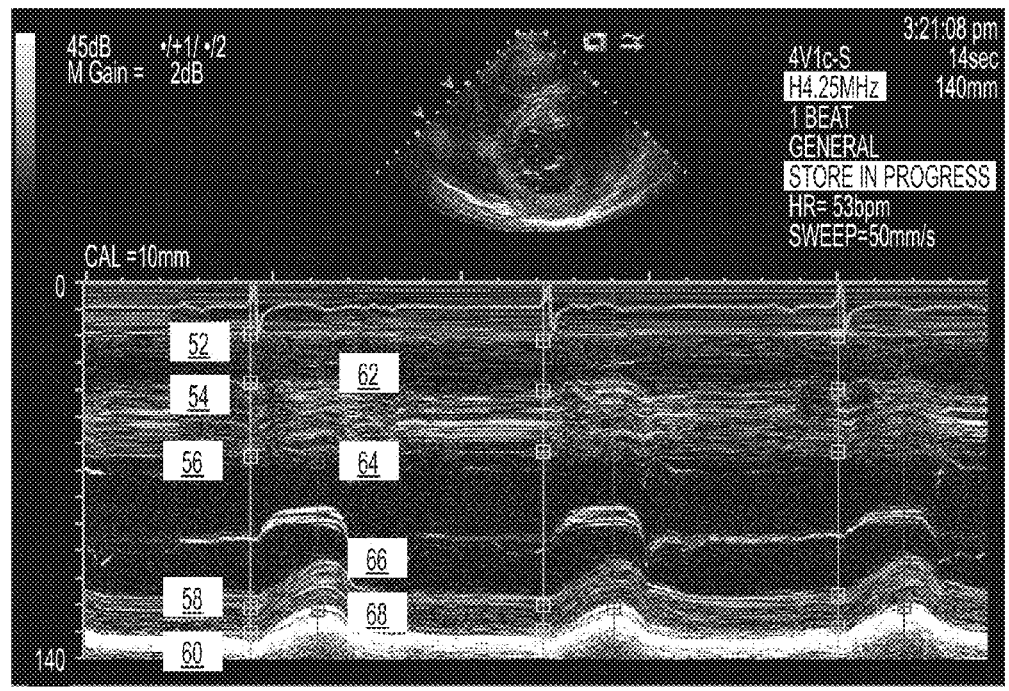
FIG. 5 is an example M-mode image, with calipers, of a left ventricle.

In act 30, the identification of the portions or initial locations is performed as a function of the locations of the other portions or initial locations. For example, the likely positions of each of the initial positions are selected with a Markov Random Field (MRF) function. The MRF function captures the geometric relationship between calipers. Any two or more structures may be used in the MRF function. For example, the structures along a given line or time use the same MRF. A different MRF is used for different times. As shown in FIG. 5, the locations for five anatomical structures (52, 54, 56, 58, and 60) are provided along an end of diastole (ED) time. Four anatomical structures (62, 64, 66, and 68) are provided along an end of systole (ES) time. Each ED line contains 5 anatomical structures (calipers), and each ES line contains 4 calipers. The B-mode image on the top illustrates the beam (dotted line) position. As another example, different MRFs are provided for different sub-sets of structures at a given time or structure locations form different times are included in the same MRF.

In one embodiment, the MRF receives a plurality of possible initial locations for each structure and a corresponding probability from the machine-trained classifier. A threshold probability is applied to limit the number of possible initial locations. The sufficiently likely locations are input to the MRF with the probabilities. The MRF outputs possible combinations of locations for groups of structures based on the input. The combinations with the highest probability are selected, such as selecting the top three or five combinations. For five combinations, five possible initial locations are provided for each structure. In alternative embodiments, the most likely candidate is selected.

Other approaches than MRF may be provided. For example, a cost function with a spring or elastic variable is used to tend the locations to an average or median location for each structure.

In act 32, the initial positions are refined to determine final positions of the structures. The initial position may be a point. The point is determined to be accurate or shifted to a more likely accurate location. The initial position may be a range of depths or points. The most likely location within the range is determined. The initial position may be a plurality of possible locations. One of the possible locations is selected. Combinations of two or more of these approaches may be used. Other refining may alternatively or additionally be used. The refinement is local by identifying positions within a limited depth range rather due to the coarse identification.

In one embodiment, the local refinement of act 32 includes four acts 34, 36, and 38 with act 36 represented two acts. Additional, different, or fewer acts may be provided, such as providing only one of the acts 34, 36, or 38, providing act 36 with just one of the operations described below, or other combinations.

In act 34, a machine-learned classifier is applied. A separate classifier is provided for each structure (e.g., nine classifiers in the example shown in FIG. 5), but joint classification or classification of a combination of structures may be provided. Each anatomy is detected independently or dependently on other detection.

The input features for this refinement classifier are Haar features from the M-mode data without or with different integration. For example, Haar features determined in two-dimensions over time and space of the M-mode data without integration are used. Other features may be used alternatively or additionally. The classifier outputs a plurality of possible locations. The final location is one of the possible locations. The outputs include location probabilities for each of the possible locations based on the input feature probabilities learned from training data. Possible locations are output for each of the structures.

The machine-learned classifier is of the same type as used in act 28. In one embodiment, a marginal space classifier trained using a probabilistic boosting cascade tree is used. Alternatively, a different type of classifier is used. Given different input features, the classifiers are different for coarse and fine searching.

The search performed by the machine-learnt classifier is constrained. A window is set based on the coarse location. For example, the portion defines the locations to be considered by a given classifier. Depths outside of the portion are not considered. As another example, an initial position output in act 22 defines the center or other location in a window. The window is a set size (e.g., predetermined in size) or may be a function of other information. For example, the window depth range or size is inversely proportional to the confidence of the initial detection result. This window is the portion of the line identified using act 22. The confidence is the probability output by the classifier for a given possible location. The probability is the location probability output by the classifier of act 28 based on the feature probabilities. Any mapping of probability to window size may be used, such as the window size being between 30 and 60 mm based on a range of probabilities (e.g., inversely linear mapped to 60-100% confidence). Other variables may be used for adapting the window size.

The output of act 34 may be one location for each structure or a plurality of possible locations for each structure with corresponding probabilities or confidence scores. The output of act 34 may be used without further processing. The most likely locations are identified as the refined or final locations. Alternatively, acts 36 and/or 38 use the output to further refine the final locations. The final locations are identified as a function of locations of other structures and/or the M-mode data, with or without further processing.

In act 36, the location of one or more structures is refined or determined as a function of other locations or other structures. For example, the positions determined in act 34 are adjusted or selected based on one or more other positions of other structures. The positions output in act 22 are used to limit the positions determined in act 34, so are indirectly used to select in act 36.

Any function may be used, such as a cost function based on ideal distances. In one embodiment, one or more MRF functions are used. The statistics about the geometric relationship of two or more structures are used to select the most likely combinations of positions of the structures. The possible locations may be input and used to limit the number of combinations. The combinations with the most likelihood may be output or used and those with the least ignored.

Using training data, the probabilities or other cost function of different geometrical relationships between certain structures are calculated. These probabilities are used to select the combination of locations for the structures. The locations of two or more structures are determined using these machine-learned functions, such as using the probabilities or other statistics. The machine-learned functions for one structure relative to another structure are used to determine locations for both structures. Different machine-learned functions may be provided for different structures, such as associated with different groupings of structures.

In one embodiment, a plurality of geometric estimation functions is applied. For example, one Markov network is used for a first group of structures, and a different Markov network is used for second group of structures. Each structure is associated with two or more of the Markov networks.

One Markov network may use the same or different structures, but at different times. Referring to FIG. 5, the structures 52, 54, 56, 62, and 64 occur at ED and ES, two different times. A Markov network is provided for this group of structures. This network is used for each of the heart cycles of interest. Another Markov network is provided for the structures 58, 60, 66, and 68. Other groupings may be provided with more or fewer groupings and corresponding Markov networks. The groupings across time enforce the position consistency of caliper positions across time.

In one embodiment, the top eleven or other number of possible positions output in act 34 for each structure are used. Using the MRF, the top three most likely combinations of positions are determined from the possible positions. Different combinations of positions may be determined and probabilities associated with each combination.

The structures are regrouped to apply other geometric cost functions. For example, the structures along each time are grouped, such as structures 52, 54, 56, 58, and 60 along the ED line being one group and structures 62, 64, 66, and 68 along the ES line being another group. A different MRF is used for each of the groups, such as MRF populated with statistics learned from training data. In one embodiment, the top three or other number of positions output for each structure by the first layer of MRF are used as inputs. This layer of geometric control enforces position consistency in a given time or across the entire depth.

If an input to a geometric relationship function does not include possible positions for a given structure, the geometric function may fail. For example, the machine-learned detector may fail to determine any locations for a given structure with sufficient probability, resulting in failure when applying the MRF.

As an alternative to failure, the geometric relationship function may assume a location with a large penalty, such as a predefined negative score for this location. The missing position or groups of possible positions for a structure are determined from the locations of the other structures, such as selecting the most likely position or positions based on the geometrical statistics alone. The locations of the structures are determined with the assumed location or locations of highest probability for the missing structure. Other processes for dealing with missing information may be used, such as determining the position of the missing structure using its average distance to the nearest neighboring structure.

The output from act 36 may be used as the final position for each structure, such as using a combination with the highest probability. Alternatively, the output from act 36 is used for further processing to determine the final position for each structure. For example, act 38 is performed.

In act 38, the M-mode data is used to determine the final position based on one or more possible positions output in acts 22, 34, or 36. A machine-learned classifier may be used with the search space limited by the input possible positions. A machine-learned classifier may be used with the possible positions input as features with features derived from the M-mode data. Other classifiers or functions may be used to determine position from M-mode data based on input of possible positions.

In one embodiment, a warping detector is used. The warping detector is a probabilistic, hierarchal, and discriminant framework for detection of anatomic structure, such as disclosed by S. K. Zhou. F. Guo, J. H. Park, G. Carneiro, J. Jackson, M. Brendel, C. Simopoulos, J. Otsuki, and D. Comaniciu in "A probabilistic, hierarchical, and discriminant (PHD) framework for rapid and accurate detection of deformable anatomic structure," International Conference on Computer Vision (ICCV), October 2007. Other detectors may be used.

The warping detector uses geometric position and M-mode data to determine position of structure. For example, the best configuration of structure positions at a time, at several times, or other groupings are determined. In one embodiment, the best configuration of positions along a given line (ED or ES) is determined separately for each line or time. The optimal configuration is selected from the fifteen or other number of likely configurations output in act 36. A machine-trained classifier uses both geometric relationship and 1D or 2D features determined from M-mode data to select a most probable configuration of the locations of structures. Both appearance (M-mode data) of the structure and the location configuration (geometric) are jointly considered. In alternative embodiments, only appearance, only configuration, or additional features are used.

In act 40, one or more measurements are performed. The measurements rely on the locations determined for the structure. The measurement values may be calculated from the ultrasound data associated with the located anatomy and/or from spatial or temporal locations associated with the anatomy. Any parameter may be calculated, such as distance, circumference, volume, change, velocity, acceleration, or other anatomy parameter. The measurement is a function of the position of one or more structures.

One dimension of the M-mode data represents space (e.g., depth) and another time, so measures of distance and/or time may be performed. For example, the measurement value is calculated as a function of a distance between two of the final positions. Example measurements include: right ventricle (RV) internal dimension in diastole (RVIDd) (e.g., difference between structures 52 and 54), interventricular septum thickness in diastole (IVSd) (e.g., difference between structures 54 and 56), left ventricle (LV) internal dimension in diastole (LVIDd) (e.g., difference between structures 56 and 58), LV posterior wall thickness in diastole (LVPWd) (e.g., difference between structures 58 and 60), interventricular septum thickness in systole (IVSs) (e.g., difference between structures 62 and 64). LV internal dimension in systole (LVIDs) (e.g., difference between structures 64 and 66), and LV posterior wall thickness in systole (LVPWs) (e.g., difference between structures 66 and 68). For aortic measurements, the AoR internal dimension in diastole (AoR), and LA internal dimension in (LA) may be calculated. Other measurements for the same or different imaging or scanning regions of the patient may be provided.

Other measurement values may be calculated. For example, one or more distances are used in estimating a volume, such as LV end diastolic volume (LVEDV), and LV end systolic volume (LVESV). The difference in volume is determined as the LV ejection fraction (LVEF).

One or more measurement values are calculated in response to user selection of a given measurement. In other embodiments, one or more measurements are automatically provided. The user activates the automatic position determination, such as selecting an appropriate application (e.g., selecting LV imaging). The appropriate, commonly used, or user defined measurements are calculated without further user input.

In act 42, information associated with one or more of the final locations is displayed. The calculated value and/or an image are displayed. The information is displayed with or without a corresponding M-mode image.

For example, a value of a measure determined based on the location is displayed. One of the measurements of act 40 is provided to the user, or a measurement from the M-mode data (e.g., a variance of intensity) at the location is provided. The value is displayed as text, in a chart, or as part of a table. The value may be labeled, such as indicating the parameter represented by the value and the units of measurement. Other information may be displayed, such as other values of measures.

Figure 6:
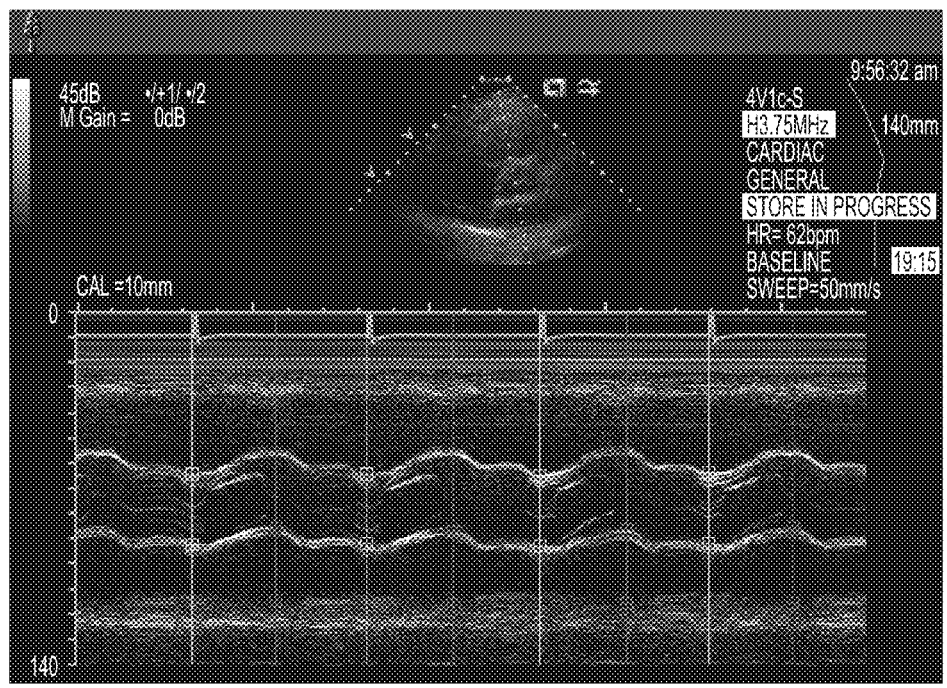
FIG. 6 is an example M-mode image, with calipers, of an aorta.

In another example, a marker is displayed to indicate the location. FIG. 6 shows an M-mode image of the aorta of a heart. A two-dimensional image is shown above the M-mode image. The two-dimensional image shows a location of the line used for the M-mode image. On the M-mode image, two calipers are shown as cross-hair boxes at both ED and ES times. Other shaped and/or sized markers may be used. The markers are the same or different for different structures. The M-mode data from which the locations are identified is used for the M-mode image, but other M-mode data may be used. FIG. 5 shows an M-mode image of the LV and RV of the heart with markers.

The method may be implemented using all of acts 22-38. For example, a dataset containing 478 or other number of M-mode images is used. 378 or other number of the M-mode images are used for training, and 100 or other number are used as the test set. As shown below in Table 1, the system may achieve accuracy in both training and test sets. The mean error over all the 478 data is 1.64 mm. The system may detect all calipers in one LV image (see FIG. 5) within 1 second. Using the warping detector of act 38 alone may uses up to 4 seconds to detect data with multiple heart cycles. The performance using exactly the same training set is: the mean error is 2.64 with standard deviation 3.73. Using the coarse-to-fine approach in acts 22-38 may provide an advantage in both accuracy and speed.

TABLE 1

The error (in millimeter) between the detection result and ground truth.

|  |  | ES | ED |
|---|---|---|---|
| Training | Mean | 1.3647 | 1.3036 |
| (378 images) | Std | 1.7989 | 1.6496 |
| Testing | Mean | 2.5695 | 2.3356 |
| (100 images) | Std | 3.6807 | 2.5060 |

Figure 7:
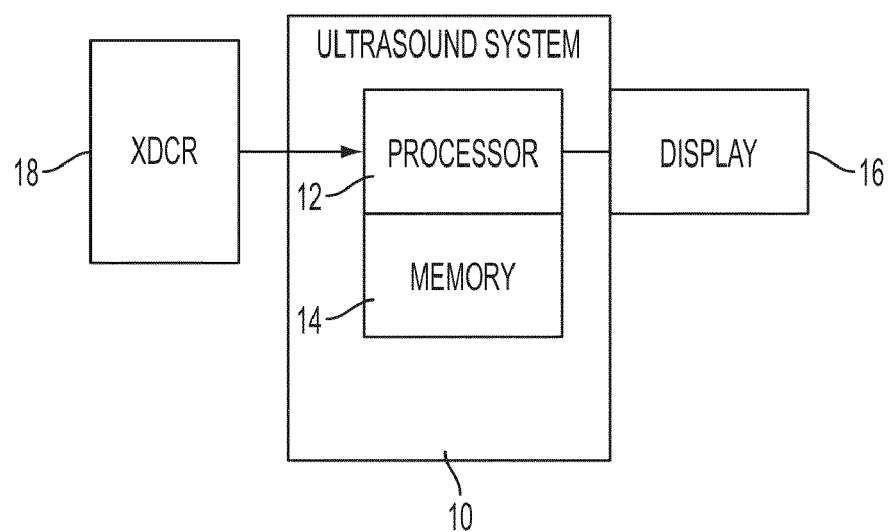
FIG. 7 is a block diagram of one embodiment of a medical ultrasound imaging system for detection of structure in ultrasound M-mode imaging.

FIG. 7 shows a medical diagnostic imaging system 10 for detection of structure in ultrasound M-mode imaging. Structures along a line may be detected, allowing measurement of the anatomies and display of the locations of the anatomy.

The system 10 is a medical diagnostic ultrasound imaging system, but may be a computer, workstation, database, server, or other system. The system 10 includes a processor 12, a memory 14, a display 16, and a transducer 18. Additional, different, or fewer components may be provided. For example, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system 10 is a workstation for off-line or later measurement of structures.

The transducer 18 is a piezoelectric or capacitive device operable to convert between acoustic and electrical energy. The transducer 18 is an array of elements, such as a one-dimensional array.

The system 10 uses the transducer 18 to scan a line, area or volume. Electrical and/or mechanical steering allows transmission and reception along different scan lines or a desired scan line.

Ultrasound data representing a line is provided in response to the scanning. The ultrasound data is beamformed, detected, and/or scan converted. The ultrasound data may be in any format, such as polar coordinate or Cartesian coordinate. The ultrasound data may be of any type, such as B-mode, flow mode, Doppler mode, contrast agent, harmonic, or other ultrasound modes of imaging. For M-mode imaging, the B-mode detector is used to sample a scan line at different times. For color M-mode imaging, the Doppler detector may be used to estimate velocities along the scan line at different times.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 is a computer readable storage medium with processing instructions. The memory 14 stores data representing instructions executable by the programmed processor 12 for detection of structure in ultrasound M-mode imaging. The instructions for implementing the processes, methods and/or techniques discussed herein are provided on computer-readable storage media or memories, such as a cache, buffer, RAM, removable media, hard drive or other computer readable storage media. Computer readable storage media include various types of non-transitory volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The memory 14 additionally or alternatively stores the ultrasound data, such as ultrasound M-mode data representing a line within the patient over a range of time. For example, the M-mode data represents a line through the left ventricle or aorta of a patient's heart. The M-mode data is at any stage of processing along the ultrasound data path. The memory 14 stores color M-mode (e.g., velocity, energy or both) and/or grayscale M-mode (e.g., intensity) ultrasound data.

For real-time imaging, the ultrasound data bypasses the memory 14, is temporarily stored in the memory 14, or is loaded from the memory 14. Real-time imaging may allow delay of a fraction of seconds, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session used to acquire the data. The imaging session is the imaging of a given patient during a given visit and/or of a given patient in a particular configuration of the system. The amount of delay between acquisition and imaging for real-time operation may vary, such as a greater delay for initially locating structure with less delay for measurements. In alternative embodiments, the ultrasound data is stored in the memory 14 from a previous imaging session and used for measuring and/or generating an M-mode image without concurrent acquisition.

The processor 12 is a general processor, digital signal processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, detecting anatomy, measuring anatomy, and/or controlling imaging.

In one embodiment, the processor 12 receives acquired ultrasound data during or after scanning and determines locations of one or more structures along the line represented by the data. The location of the structure is determined at one time or at different times. For example, the location of a given structure is determined one or two times for every heart cycle. The processor 12 performs or controls other components to perform the methods described herein.

The system 10 may include a user input, such as for configuring the system 10 and/or activation operations. The processor 12 may identify locations of structure in M-mode data free of user input of any location of any structure along the line. The user may refine the final locations output by the processor 12, but the processor 12 determines the locations without any initial location indication. Alternatively, the user inputs location information during the process to identify the location.

The processor 12 performs machine learning and/or applies one or more machine-learnt algorithms. For example, the processor 12 applies a probabilistic model to detect anatomy, to detect locations of anatomy, to determine geometrical relationships, or for other functions. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. In one embodiment, a marginal space learning framework is determined using a probabilistic boosting cascade tree framework. The classifier is instructions, a matrix, a learned code, or other software and/or hardware for distinguishing between information in a medical image.

Different classifiers may be trained for different purposes, such as for use with different input features, different structures, different line locations, different structure groupings, and/or different stages of processing. The classifier may include a plurality of models or classifiers (e.g., detectors) operable together or independently. For example, different probabilistic models are trained for different anatomy. The probabilistic models may be joint or dependent. The location of other anatomies is used to limit or define a search space for a current anatomy and/or as a feature input for classification of another anatomy.

The different classifiers for different purposes or structures are the same or different types of classifiers. The same or different types of classifiers may be used for the same type of classification, such as different types of classifiers being used for different marginal space classification (e.g., the classifier for coarse detection is different than the classifier for refining the locations).

In one embodiment, the probabilistic model is formed from a plurality of probabilistic boosting tree classifiers. Separate training and resulting machine-trained classifiers are provided for each anatomy of interest. For each of these separate classifiers, separate probabilistic boosting tree classifiers are provided for each of the marginal space types. For example, the classifiers follow the marginal space learning protocol, providing a position detector using Haar wavelet features. Separate marginal space classifiers are provided for each structure, purpose and/or stage of processing. For example, each detector is a probabilistic boosting tree with 5 levels, and each node in the tree is a strong classifier with at most 30 weak classifiers. Any number of classifiers, nodes, levels, or other combinations may be used.

For application, the processor 12 calculates features for classification. The same or different features are used for classification in each stage. The features are one-dimensional, two-dimensional (e.g., space and time) or other features. Using a machine-trained translation classifier, the features are used to rule out hypotheses and/or determine the most likely locations for structures.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task.

In one embodiment, the processor 12 identifies a given location by first finding a range or plurality of possibilities. A machine-trained model is applied to determine the initial depths or range. The final location is determined from the range of initial depths. Another machine-trained model is applied to determine the final location. One or both of finding the range and determining the final location is performed using geometric information or information about locations for other structures. For example, a Markov field of other locations relative to the given location is applied in both the coarse and fine location determinations. The Markov field may be applied even where one or more expected structures is not indicated. The Markov field is used to estimate the missing location.

The processor 12 calculates measurements of the detected anatomy. Any measurement may be made. In one embodiment, the classifier is trained with measurement annotations, such as caliper positions. The detection of the anatomy provides the caliper positions as an output of the classifier. The measurement corresponding to the caliper position is performed, such as measuring a distance, volume, or ejection fraction. Any now known or later developed measurement may be used.

The display 16 is a CRT, LCD, plasma, projector, printer, or other output device for showing an image. The display 16 displays an image, such as an M-mode image. The M-mode data representing the line is used for generating the image, such as a color M-mode or grayscale M-mode image. The M-mode image is generated with the location of detected structures indicated by markers. The M-mode image represents return along a line over time. For each desired time, the determined location is indicated by a marker.

Alternatively or additionally, a value of the measurement is displayed. The value may be displayed in a chart, graph, and/or on an image. The measurements that are a function of the locations are displayed. Only one or a plurality of different measurement may be displayed. The values may be displayed with the corresponding M-mode image. The measurements corresponding to the values may be displayed on the M-mode image, such as overlaying an indication of what the measurement represents.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for detection of structure in ultrasound M-mode imaging, the method comprising:
    acquiring M-mode data representing a line within a patient over a range of time;
    identifying a first portion of the line as associated with a first anatomical structure of a heart of the patient as a rough estimate, the first portion comprising a first plurality of depths, the identifying being a function of the M-mode data;
    identifying constrained by the rough estimate a first location of the first anatomical structure within the first portion, a search for the identifying of the first location being limited to the first portion; and
    displaying information associated with the first location.

2. The method of claim 1 wherein identifying the first portion comprises:
    integrating the M-mode data over time for each depth of the line; and
    identifying the first portion from the integrated M-mode data.

3. The method of claim 1 wherein identifying the first portion comprises applying a machine-learned classifier.

4. The method of claim 1 further comprising:
    identifying at least a second portion of the line as associated with at least a second structure of the heart of the patient, the second portion comprising a second plurality of depths, the second plurality including or not including one or more of the depths of the first plurality;
    wherein identifying the first portion comprises identifying as a function of the second portion.

5. The method of claim 1 further comprising:
    identifying at least a second portion of the line as associated with at least a second structure of the heart of the patient, the second portion comprising a second plurality of depths, the second plurality including or not including one or more of the depths of the first plurality;
    wherein identifying the first location comprises applying a first machine-learned classifier, the first location being one of a plurality of possible first locations output by the first machine-learned classifier;
    further comprising:
    identifying a second location of the second structure within the second portion with a second machine-learned classifier, the second location being one of a plurality of possible second locations output by the second machine-learned classifier;
    wherein identifying the first and second locations further comprises determining the first location as a machine-learned function of the second location and determining the second location as a machine-learned function of the first location.

6. The method of claim 1 wherein identifying the first location comprises identifying as a function of other locations of other structure and the M-mode data.

7. The method of claim 1 wherein identifying the first portion and identifying the first location are performed without user input of any location along the line.

8. The method of claim 1 wherein identifying the first location comprises identifying as a function of other locations of other structure, the identifying operable with a missed one of the other locations such that the missed one of the other locations is determined from the identified first location and identified ones of the other locations.

9. The method of claim 1 wherein displaying information associated with the first location comprises displaying the first location as a marker in an M-mode image generated from the M-mode data.

10. The method of claim 1 wherein displaying information associated with the first location comprises displaying a measure determined as a function of the first location.

11. In a non-transitory computer readable storage medium having stored therein data representing instructions executable by a programmed processor for detection of structure in ultrasound M-mode imaging, the storage medium comprising instructions for:
    locating, in an M-mode image, first positions of respective structures in a search, the search being based on a profile curve of intensity as a function of depth integrated over a plurality of times such that the profile curve is a function of M-mode data from both different times and depths and machine-trained feature probabilities;
    refining the first positions to second positions of the structures, the refining limited by the first positions, each of the second positions being a function of a plurality of the first positions; and
    calculating a measurement as a function of the second positions;

wherein the locating and refining are performed free of user input of a location of any structure in the M-mode image.

12. The non-transitory computer readable storage medium of claim 11 wherein locating the first positions comprises determining ranges for each of the first positions as a function of respective first marginal space classifiers and selecting likely positions of each of the first positions with a Markov Random Field function.

13. The non-transitory computer readable storage medium of claim 11 wherein refining comprises:
limiting the second positions within ranges that are inversely proportional to location probabilities determined as a function of the machine-trained feature probabilities; and
applying a Markov network.

14. The non-transitory computer readable storage medium of claim 13 wherein applying the Markov network comprises applying a first Markov network based on the second positions at different times in the M-mode image and applying a second Markov network based on the second positions at a same time in the M-mode image.

15. The non-transitory computer readable storage medium of claim 11 wherein refining comprises applying at least one Markov network and detecting the second positions as a function of possible configurations output by the Markov network and the M-mode image.

16. The non-transitory computer readable storage medium of claim 11 further comprising indicating caliper positions at the second positions in the M-mode image.

17. The non-transitory computer readable storage medium of claim 11 wherein calculating the measurement comprises calculating as a function of a distance between two of the second positions.

18. A system for detection of structure in ultrasound M-mode imaging, the system comprising:
a memory operable to store ultrasound M-mode data representing a line within a patient over a range of time;
a processor operable to identify a location of the structure from the ultrasound M-mode data and free of user input of any location of any structure along the line; and
a display operable to display an M-mode image of the line with the location indicated by a marker, to display a measurement that is a function of the location, or to display the M-mode image of the line with the marker and the measurement;
wherein the processor is operable to identify the location by finding a depth range of possibilities as a function of a first machine-trained model, the depth range being less than all depths, and determine the location as within the range and with a second machine-trained model, at least one of finding the range and determining the location being a function of a Markov field of other locations relative to the location.

19. The system of claim 18 wherein the processor is operable to determine the location as the function of the Markov field of other locations where one of the other locations is missing and is operable to determine the one of the other locations as a function of the determined location.

* * * * *